United States Patent [19]

LaRusso

[11] Patent Number: 5,583,104
[45] Date of Patent: Dec. 10, 1996

[54] TREATMENT OF PROLIFERATION OF BILE DUCT EPITHELIUM

[75] Inventor: Nicholas F. LaRusso, Rochester, Minn.

[73] Assignee: Mayo Foundation for Medical Research and Education, Rochester, Minn.

[21] Appl. No.: 163,277

[22] Filed: Dec. 6, 1993

[51] Int. Cl.$^6$ .................................................. A61K 38/00
[52] U.S. Cl. ................................................. 514/11; 514/2
[58] Field of Search ........................................... 514/11, 2

[56] References Cited

FOREIGN PATENT DOCUMENTS

0450480A2  10/1991  European Pat. Off. .
2241167A    8/1991  United Kingdom .

OTHER PUBLICATIONS

Tracy, T. et al American Journal of Pathology vol. 143 No. 6 Dec. 1993.
Zalatnai et al., "Responsiveness of the Hamster Pancreatic Cancer to Treatment with Microcapsules of D–Trp–6–LH–RH and Somatostatin Analog RC–160", International Journal of Pancreatology, 4:149–160, 1989.
"Somatostatin Anaglogue (Octreotide) Inhibits Bile Duct Epithelial Cell Proliferation and Fibrosis After Extrahepatic Biliary Obstruction" Thomas F. Tracey et al., American Journal of Pathology, 1993.
"Pancreas and Hepatobiliary Tract", Leonard L. Gunderson et al., Atlas of Human Anatomy, Ed. 9, vol, 2, 1977.
"Research into the Results of Resection of Hilar Bile Duct Cancer", Egge. J. Boerman, Surgery, vol. 108, No. 2, Sep. 1990.
"Primary Hepatic Malignancy: the role of liver transplantation", Vr. J. Surgery, vol. 77, Sep. 1990, pp. 983–987.
"Experience with transplantation in the treatment of liver cancer", Career Chemother Pharmacol, vol. 23, 1989, pp. 104–109.
"Characterisation of Three New Human Tumor Cell Lines", Journal of Hepatology, Knuth et al. 1985, vol. 1 pp. 579–596.
"The Role of Somatostatin and Its Analogs in the Diagnosis and Treatment of Tumors", Lamberts et al., Somatostatin Role in Tumor Treatment and Diagnosis, vol. 12, No. 4, Nov. 1991.
"Biliary Tract Obstruction Secondary to Cancer: Management Guidelines and Selected Literature Review", Journal of Clinical Oncology, vol. 5, No. 6, 1987, pp. 969–981.
"Carcinoma of the Gallbladder and Extrahepatic Bile Ducts", David Nagorney et al., Seminars in Oncology, vol. 15, No. 2, Apr. 1988, pp. 106–115.
"Liver Transplantation for Malignant Disease", O'Grady et al., Ann. Surg., vol. 207, No. 4, Apr. 1988.
"Hepatis transplantation for primary and metastatic cancers of the liver", Israel Penn, Surgery, Oct. 1991, vol. 110, No. 4.
"The Role of Liver Transplantation in Hepatobiliary Malignancy", B. Ringe et al. Ann. Surg. Jan. 1989, vol., 209, No. 1.
"Direct Inhibitory Effects of Somatostatin (Analogues) on the Growth of Human Breast Cancer Cells", Setyono–Han et al., Cancer Research , vol. 47, Mar. 1987, pp. 1566–1570.
"Cholangiocarcinoma", Charles J. Yeo et al., Surgical Clinics of North America, vol. 70, No. 6, Dec. 1990.

Primary Examiner—Paul J. Killos
Attorney, Agent, or Firm—Fish & Richardson P.C., P.A.

[57] ABSTRACT

A method of inhibiting proliferation of bile duct epithelium, said method comprising the step of contacting said epithelium with an effective amount of somatostatin or a somatostatin agonist.

18 Claims, 2 Drawing Sheets

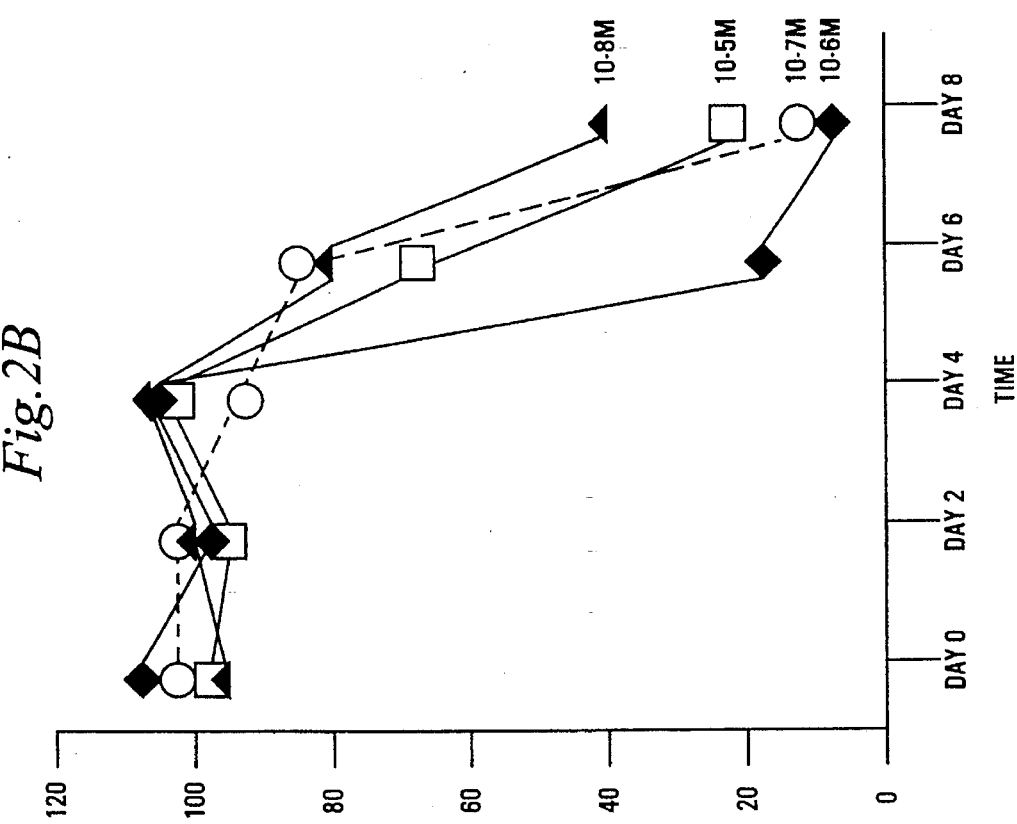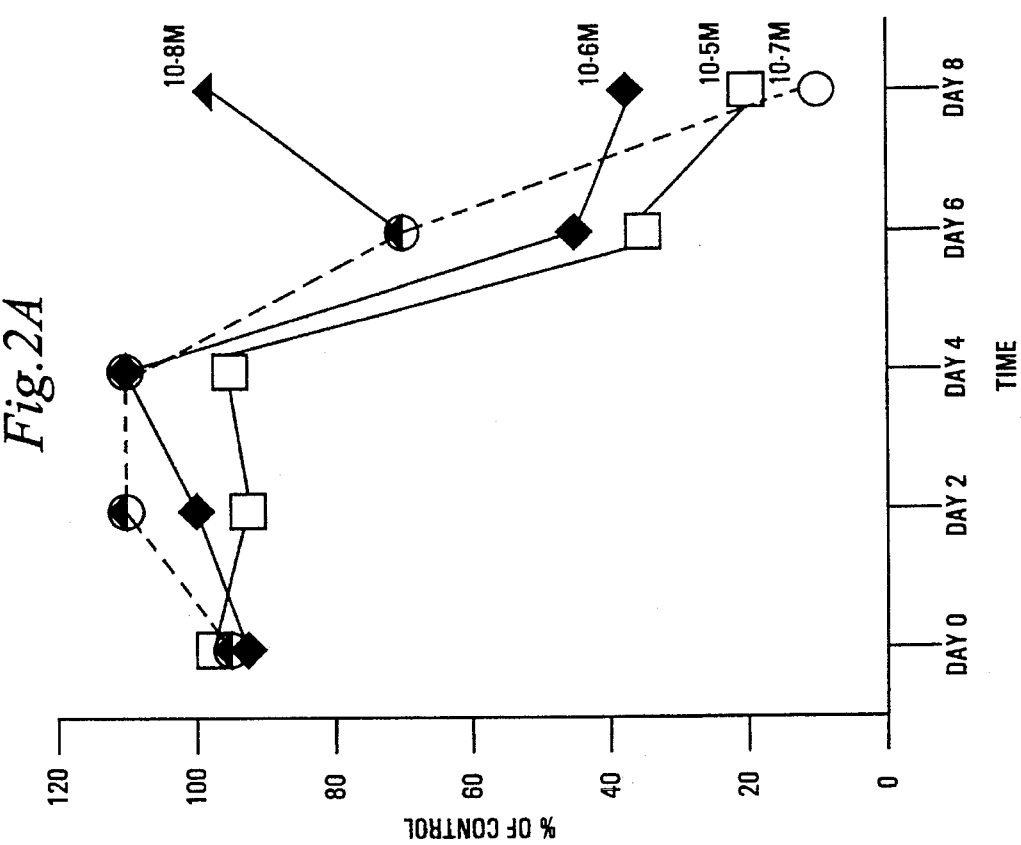

TREATMENT OF PROLIFERATION OF BILE DUCT EPITHELIUM

FIELD OF THE INVENTION

This invention relates to a method of inhibiting the growth of benign or malignant tumor.

BACKGROUND OF THE INVENTION

Cholangiocarcinoma refers to any malignancy originating in the intra- or extrahepatic bile ducts. These tumors probably represent 10–15% of primary hepatobiliary cancers, and their incidence in the United States is estimated at up to 3,000 per year. See Yeo et al. Surg. Clin. North Amer. 70:1429 (1990); Vogt et al. Oncology 2:37 (1988). The prognosis for these tumors is universally dismal, with a majority of patients dying within six months to one year of diagnosis. See Imrie et al. Wright's Liver and Biliary Diseases, Vol 2, 3d ed., p. 1516 (1992).

Cholangiocarcinomas are notoriously difficult to diagnose. The diagnosis is usually performed by non-invasive imaging studies (e.g., ultrasound or CT scan) with an overall accuracy of only about 50%. Positive histology is required for absolute diagnosis, and this is most effectively performed by fine needle aspiration biopsy. Desa et al. Gut 32(10):1188 (1991); Bedrossian et al. Arch. Patho. Lab. Med. 113(11):1225 (1989). However, by the time this diagnosis is made, the disease has commonly reached the point where curative surgical therapy is impossible. Yeo et al. Cholangiocarcinoma (Review) Surg. Clin. North Amer. 70:1429 (1990); Miyazaki et al. Surg. Ther. 56:443 (1987).

Surgical resection presently provides the best hope for cure. Only ten percent of patients with cholangiocarcinomas, however, are surgically treatable because of the location of their tumors. See Nargoney et al., Sem. Oncol. 15:106 (1988). Even after resection, twenty-five percent of these patients will still have residual tumors, and the five year survival rate for resected patients is only thirteen percent with an operative mortality up to twelve percent. See Yeo et al., Surg. Clin. North Amer. 70:1429 (1990); Boerma et al., Surgery 215:31 (1990).

The possibility of liver transplantation has also been attempted as a potential treatment modality. This treatment, however, has generally been unsuccessful since the recurrence of cholangiocarcinomas is virtually 100%. The survivorship, therefore, appears to be no better than that of the untreated patient. See Penn et al., Surgery 110:726 (1991); Jenkins et al., Cancer Chemother. Pharmac. 23:S104 (1989). Many liver transplant centers have abandoned transplantation of patients with cholangiocarcinomas. Other centers consider transplantations for cholangiocarcinoma to be experimental in nature. In some centers, protocols employing adjuvant chemotherapy and/or radiation therapy in conjunction with transplantation are under investigation.

Non-surgical therapy of cholangiocarcinomas has been limited to patients who are found to be unresectable on the basis of either preoperative imaging or surgical exploration. Current modalities generally include variations of radiation therapy (e.g., external radiation with or without chemotherapy or the combination of external radiation or intraluminal brachytherapy). Although external irradiation with or without chemotherapy may lead to prolonged survival in some patients, the side effects of these forms of therapy are often severe as the nearby liver, gut, and spinal cord are irradiated as well. See Gunderson et al, Principles and Practice of Radiation Oncology p. 985 (1992). Palliative stenting helps to relieve the symptoms of cholangitis, but sepsis may occur in up to 88% or percutaneous stents. See Lokich et al, J. Clin Oncol. 5:969 (1987).

SUMMARY OF THE INVENTION

The present invention relates to a method for inhibiting benign or malignant proliferation of bile duct epithelium. The method includes the step of contacting the proliferating epithelial cells with an effective amount of somatostatin or a somatostatin agonist. It is preferred that the contacting step be effected parenterally, e.g., administered to the proliferation site in a subject intravenously, subcutaneously, by implantation (e.g., near the liver) or by perfusion (e.g., of the liver). Delivery of drug by implantation is well known in the art, see, e.g., U.S. Pat. Nos. 4,675,189 and 4,767,628, both of which are hereby incorporated by reference.

In the present disclosure, any malignant proliferation of bile duct epithelium is also called cholangiocarcinoma.

Both definition and exemplification of "somatostatin agonist" appear below.

A therapeutically effective amount depends upon the condition being treated, the route of administration chosen, and the specific activity of the compound used, and ultimately will be decided by the attending physician or veterinarian.

While it is possible for the somatostatin analog to be administered as the pure or substantially pure compound, it is preferable to present it as a pharmaceutical formulation or preparation.

The formulations to be used in the present invention, for both humans and animals, comprise any of the octapeptide analogs to be described below, together with one or more pharmaceutically acceptable carriers therefor, and optionally other therapeutic ingredients.

The carrier must be "acceptable" in the sense of being compatible with the active ingredient(s) of the formulation (and preferably, capable of stabilizing peptides) and not deleterious to the subject to be treated. Desirably, the formulation should not include oxidizing agents or other substances with which peptides are known to be incompatible. For example, somatostatin analogs in the cyclized form are oxidized; thus, the presence of reducing agents as excipients could lead to an opening of the cystine disulfur bridge. On the other hand, highly oxidative conditions can lead to the formation of cysteine sulfoxide and to the oxidation of tryptophane. Consequently, it is important to carefully select the excipient. As pointed out previously, pH is another key factor and it is necessary to buffer the product under slightly acidic conditions (pH 5 to 6).

The formulations may conveniently be presented in unit dosage form and may be prepared by any of the methods well known in the art of pharmacy. All methods include the step of bringing the active ingredient(s) into association with the carrier which constitutes one or more accessory ingredients.

In general, the formulations for tablets or powders are prepared by uniformly and intimately blending the active ingredient with finely divided solid carriers, and then, if necessary as in the case of tablets, forming the product into the desired shape and size.

Formulations suitable for intravenous administration, on the other hand, conveniently comprise sterile aqueous solutions of the active ingredient(s). Preferably, the solutions are isotonic with the blood of the subject to be treated. Such formulations may be conveniently prepared by dissolving solid active ingredient(s) in water to produce an aqueous solution, and rendering said solution sterile. The formulation may be presented in unit or multi-dose containers, for example, sealed ampoules or vials.

Other features and advantages of the invention will be apparent from the following description of the preferred embodiments thereof, and from the claims.

Abbreviations

β-Nal=β-naphthylalanine
β-Pal=β-pyridylalanine
hArg(Bu)=N-guanidino-(butyl)-homoarginine
hArg(Et)$_2$=N, N'-guanidino-(diethyl)-homoarginine
hArg(CH$_2$CF$_3$)$_2$=N, N'-guanidino-bis-(2,2,2,-trifluoroethyl)homoarginine
hArg(CH$_3$, hexyl)=N, N'-guanidino-(methyl, hexyl)homoarginine
Lys(Me)=N$^\epsilon$-methyllysine
Lys(iPr)=N$^\epsilon$-isopropyllysine
AmPhe=aminomethylphenylalanine
AChxAla=aminocyclohexylalanine
Abu=α-aminobutyric acid
Tpo=4-thiaproline
MeLeu=N-methylleucine
Orn=ornithine
Nle=norleucine
Nva=norvaline
Trp(Br)=5-bromo-tryptophan
Trp(F)=5-fluoro-tryptophan
Trp(NO$_2$)=5-nitro-tryptophan
Gaba=γ-aminobutyric acid
Bmp=β-mercaptopropionyl
Ac=acetyl
Pen=pencillamine

DESCRIPTION OF THE PREFERRED EMBODIMENTS

DRAWINGS: BRIEF DESCRIPTION

The drawings will first be briefly described.

Figure 1B:
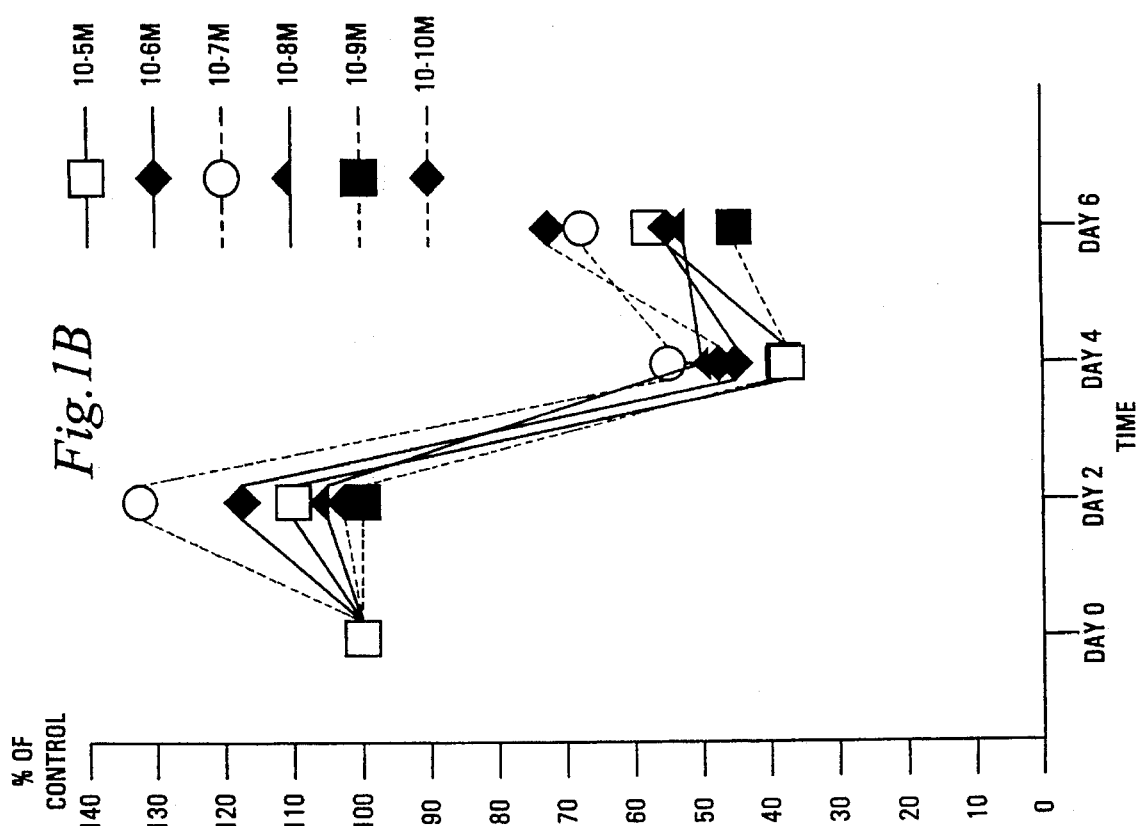
Figure 1A:
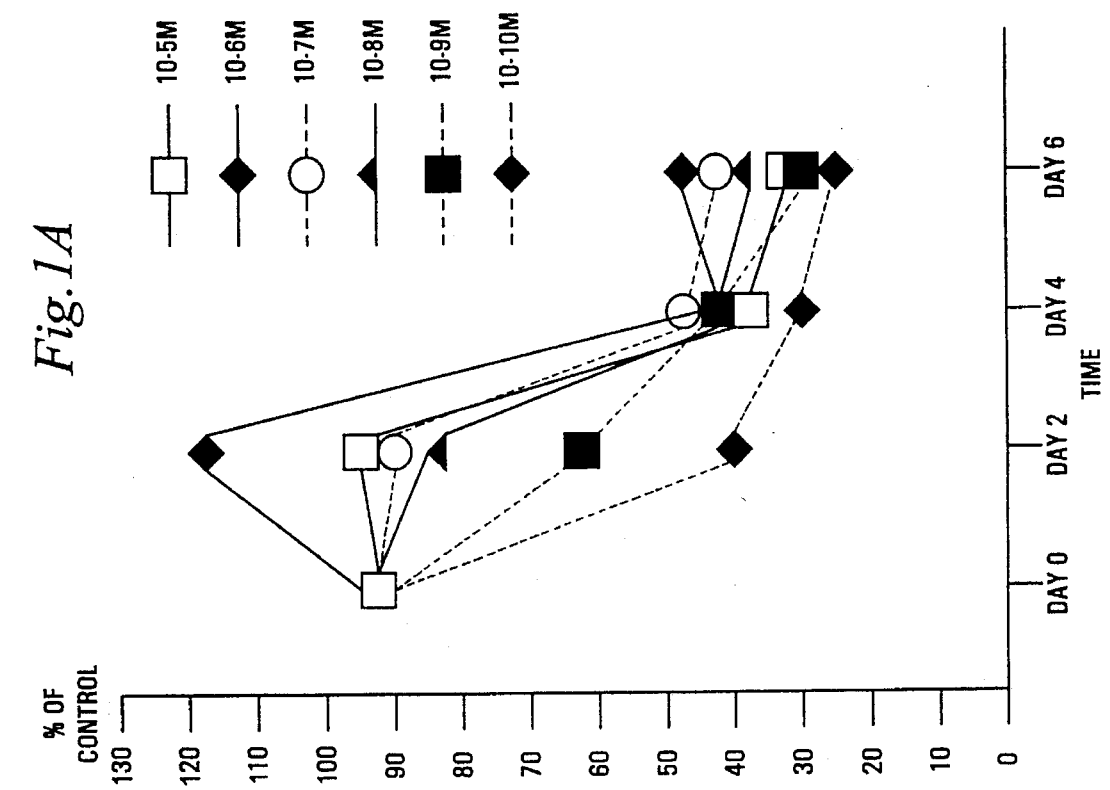

FIGS. 1 and 2 are graphs showing the growth inhibitory effects of somatostatin and a somatostatin analog on a cholangiocarcinoma cell line.

Somatostatin and Its Agonists

Somatostatin (somatotropin release inhibiting factor, or SRIF) is an inhibitor of secretion of the growth hormone and was originally isolated from the hypothalamus. Brazeau et al., Science 179:77 (1973). Somatostatin has a broad spectrum of biological effects, participates in a high number of biological processes and in the majority of cases, plays the role of an inhibitory factor (e.g., it inhibits the release of prolactin, insulin, glucagon, gastrin, secretin, and cholecystokinin). Reichlin, Somatostatin, N. Eng. J. Med. 309:1495 and 1556 (1983).

Native somatostatin has a very short duration of effect in vivo since it is rapidly inactivated by endo- and exopeptidase. Many novel analogs have been prepared in order to enhance the duration of effect, biological activity, and selectivity of this hormone. Such analogs will be called somatostatin agonists herein.

Somatostatin agonists which can be used to practice the therapeutic method of the present invention include, but are not limited to, those covered by formulas or those specifically recited in the publications set forth below, all of which are hereby incorporated by reference.

EP Application 0 505 680 A1 (1992);
Van Binst, G. et al. Peptide Research 5:8 (1992);
Horvath, A. et al. Abstract, "Conformations of Somatostatin Analogs Having Antitumor Activity", 22nd European peptide Symposium, Sep. 13–19, 1992, Interlaken, Switzerland;
PCT Application WO 91/09056 (1991);
EP Application 0 363 589 A2 (1990);
U.S. Pat. No. 4,904,642 (1990);
U.S. Pat. No. 4,871,717 (1989);
U.S. Pat. No. 4,853,371 (1989);
U.S. Pat. No. 4,725,577 (1988);
U.S. Pat. No. 4,684,620 (1987)
U.S. Pat. No. 4,650,787 (1987);
U.S. Pat. No. 4,603,120 (1986);
U.S. Pat. No. 4,585,755 (1986);
EP Application 0 203 031 A2 (1986);
U.S. Pat. No. 4,522,813 (1985);
U.S. Pat. No. 4,486,415 (1984);
U.S. Pat. No. 4,485,101 (1984);
U.S. Pat. No. 4,435,385 (1984);
U.S. Pat. No. 4,395,403 (1983);
U.S. Pat. No. 4,369,179 (1983);
U.S. Pat. No. 4,360,516 (1982);
U.S. Pat. No. 4,358,439 (1982);
U.S. Pat. No. 4,328,214 (1982);
U.S. Pat. No. 4,316,890 (1982);
U.S. Pat. No. 4,310,518 (1982);
U.S. Pat. No. 4,291,022 (1981);
U.S. Pat. No. 4,238,481 (1980);
U.S. Pat. No. 4,235,886 (1980);
U.S. Pat. No. 4,224,190 (1980);
U.S. Pat. No. 4,211,693 (1980);
U.S. Pat. No. 4,190,648 (1980);
U.S. Pat. No. 4,146,612 (1979); and
U.S. Pat. No. 4,133,782 (1979).

Preferred somatostatin agonists include, but are not limited to, the following somatostatin analogs which are disclosed in the above-cited references:

H-D-β-Nal-Cys-Tyr-D-Trp-Lys-Thr-Cys-Thr-NH2
H-D-Phe-Cys-Phe-D-Trp-Lys-Thr-Cys-β-Nal-NH2
H-D-Phe-Cys-Tyr-D-Trp-Lys-Thr-Cys-β-Nal-NH2
H-D-β-Nal-Cys-Phe-D-Trp-Lys-Thr-Cys-Thr-NH2
H-D-Phe-Cys-Tyr-D-Trp-Lys-Thr-Pen-Thr-NH2
H-D-Phe-Cys-Phe-D-Trp-Lys-Thr-Pen-Thr-NH2
H-D-Phe-Cys-Tyr-D-Trp-Lys-Thr-Pen-Thr
H-D-Phe-Cys-Phe-D-Trp-Lys-Thr-Pen-Thr
H-Gly-Pen-Phe-D-Trp-Lys-Thr-Cys-Thr
H-Phe-Pen-Tyr-D-Trp-Lys-Thr-Cys-Thr
H-Phe-Pen-Phe-D-Trp-Lys-Thr-Pen-Thr
H-D-Phe-Cys-Phe-D-Trp-Lys-Thr-Cys-threoninol;

H-D-Phe-Cys-Phe-D-Trp-Lys-Thr-Cys-Thr-NH$_2$;
H-D-Trp-Cys-Tyr-D-Trp-Lys-Val-Cys-Thr-NH$_2$;
H-D-Trp-Cys-Phe-D-Trp-Lys-Thr-Cys-Thr-NH$_2$;
H-D-Phe-Cys-Tyr-D-Trp-Lys-Val-Cys-Thr-NH$_2$;
H-D-Phe-Cys-Tyr-D-Trp-Lys-Val-Cys-Trp-NH$_2$;
H-D-Phe-Cys-Tyr-D-Trp-Lys-Val-Cys-Thr-NH$_2$;
Ac-D-Phe-Lys*-Tyr-D-Trp-Lys-Val-Asp-Thr-NH$_2$ (an amide bridge formed between Lys* and Asp);
Ac-hArg(Et)$_2$-Gly-Cys-Phe-D-Trp-Lys-Thr-Cys-Thr-NH$_2$;
Ac-D-hArg(Et)$_2$-Gly-Cys-Phe-D-Trp-Lys-Thr-Cys-Thr-NH$_2$;
Ac-D-hArg(Bu)-Gly-Cys-Phe-D-Trp-Lys-Thr-Cys-Thr-NH$_2$;
Ac-D-hArg(Et)$_2$-Cys-Phe-D-Trp-Lys-Thr-Cys-Thr-NH$_2$;
Ac-L-hArg(Et)$_2$-Cys-Phe-D-Trp-Lys-Thr-Cys-Thr-NH$_2$;
Ac-D-hArg(CH$_2$CF$_3$)$_2$-Cys-Phe-D-Trp-Lys-Thr-Cys-Thr-NH$_2$;
Ac-D-hArg(CH$_2$CF$_3$)$_2$-Gly-Cys-Phe-D-Trp-Lys-Thr-Cys-Thr-NH$_2$;
Ac-D-hArg(CH$_2$CF$_3$)$_2$-Gly-Cys-Phe-D-Trp-Lys-Thr-Cys-Phe-NH$_2$;
Ac-D-hArg(CH$_2$CF$_3$)$_2$-Gly-Cys-Phe-D-Trp-Lys-Thr-Cys-Thr-NHEt;
Ac-L-hArg(CH$_2$-CF$_3$)$_2$-Gly-Cys-Phe-D-Trp-Lys-Thr-Cys-Thr-NH$_2$;
Ac-D-hArg(CH$_2$CF$_3$)$_2$-Gly-Cys-Phe-D-Trp-Lys(Me)-Thr-Cys-Thr-NH$_2$;
Ac-D-hArg(CH$_2$CF$_3$)$_2$-Gly-Cys-Phe-D-Trp-Lys(Me)-Thr-Cys-Thr-NHEt;
Ac-hArg(CH$_3$, hexyl)-Gly-Cys-Phe-D-Trp-Lys-Thr-Cys-Thr-NH$_2$;
H-hArg(hexyl)$_2$-Gly-Cys-Phe-D-Trp-Lys-Thr-Cys-Thr-NH$_2$;
Ac-D-hArg(Et)$_2$-Gly-Cys-Phe-D-Trp-Lys-Thr-Cys-Thr-NHEt;
Ac-D-hArg(Et)$_2$-Gly-Cys-Phe-D-Trp-Lys-Thr-Cys-Phe-NH$_2$;
Propionyl-D-hArg(Et)$_2$-Gly-Cys-Phe-D-Trp-Lys(iPr)-Thr-Cys-Thr-NH$_2$;
Ac-D-β-Nal-Gly-Cys-Phe-D-Trp-Lys-Thr-Cys-Gly-hArg(Et)$_2$-NH$_2$;
Ac-D-Lys(iPr)-Gly-Cys-Phe-D-Trp-Lys-Thr-Cys-Thr-NH$_2$;
Ac-D-hArg(CH$_2$CF$_3$)$_2$-D-hArg(CH$_2$CF$_3$)$_2$-Gly-Cys-Phe-D-Trp-Lys-thr-Cys-Thr-NH$_2$;
Ac-D-hArg(CH$_2$CF$_3$)$_2$-D-hArg(CH$_2$CF$_3$)$_2$-Gly-Cys-Phe-D-Trp-Lys-Thr-Cys-Phe-NH$_2$;
Ac-D-hArg(Et)$_2$-D-hArg(Et)$_2$-Gly-Cys-Phe-D-Trp-Lys-Thr-Cys-Thr-NH$_2$;
Ac-Cys-Lys-Asn-4-Cl-Phe-Phe-D-Trp-Lys-Thr-Phe-Thr-Ser-D-Cys-NH$_2$;
Bmp-Tyr-D-Trp-Lys-Val-Cys-Thr-NH$_2$;
Bmp-Tyr-D-Trp-Lys-Val-Cys-Phe-NH$_2$;
Bmp-Tyr-D-Trp-Lys-Val-Cys-p-Cl-Phe-NH$_2$;
Bmp-Tyr-D-Trp-Lys-Val-Cys-β-Nal-NH$_2$
H-D-β-Nal-Cys-Tyr-D-Trp-Lys-Val-Cys-Thr-NH$_2$;
H-D-Phe-Cys-Tyr-D-Trp-Lys-Abu-Cys-Thr-NH$_2$;
H-D-Phe-Cys-Tyr-D-Trp-Lys-Abu-Cys-β-Nal-NH$_2$;
H-pentafluoro-D-Phe-Cys-Tyr-D-Trp-Lys-Val-Cys-Thr-NH$_2$;
Ac-D-β-Nal-Cys-pentafluoro-Phe-D-Trp-Lys-Val-Cys-Thr-NH$_2$;
H-D-β-Nal-Cys-Tyr-D-Trp-Lys-Val-Cys-β-Nal-NH$_2$;
H-D-Phe-Cys-Tyr-D-Trp-Lys-Val-Cys-β-Nal-NH$_2$;
H-D-β-Nal-Cys-Tyr-D-Trp-Lys-Abu-Cys-Thr-NH$_2$;
H-D-p-Cl-Phe-Cys-Tyr-D-Trp-Lys-Abu-Cys-Thr-NH$_2$;
Ac-D-p-Cl-Phe-Cys-Tyr-D-Trp-Lys-Abu-Cys-Thr-NH$_2$;
H-D-Phe-Cys-β-Nal-D-Trp-Lys-Val-Cys-Thr-NH$_2$;
H-D-Phe-Cys-Tyr-D-Trp-Lys-Cys-Thr-NH$_2$;
cyclo (Pro-Phe-D-Trp-N-Me-Lys-Thr-Phe);
cyclo (Pro-Phe-D-Trp-N-Me-Lys-Thr-Phe);
cyclo (Pro-Phe-D-Trp-Lys-Thr-N-Me-Phe);
cyclo (N-Me-Ala-Tyr-D-Trp-Lys-Thr-Phe);
cyclo (Pro-Tyr-D-Trp-Lys-Thr-Phe);
cyclo (Pro-Phe-D-Trp-Lys-Thr-Phe);
cyclo (Pro-Phe-L-Trp-Lys-Thr-Phe); (SEQ ID NO:1)
cyclo (Pro-Phe-D-Trp(F)-Lys-Thr-Phe); (SEQ ID NO:2)
cyclo (Pro-Phe-Trp(F)-Lys-Thr-Phe); (SEQ ID NO:3)
cyclo (Pro-Phe-D-Trp-Lys-Ser-Phe);
cyclo (Pro-Phe-D-Trp-Lys-Thr-p-Cl-Phe);
cyclo (D-Ala-N-Me-D-Phe-D-Thr-D-Lys-Trp-D-Phe);
cyclo (D-Ala-N-Me-D-Phe-D-Val-Lys-D-Trp-D-Phe);
cyclo (D-Ala-N-Me-D-Phe-D-Thr-Lys-D-Trp-D-Phe);
cyclo (D-Abu-N-Me-D-Phe-D-Val-Lys-D-Trp-D-Tyr);
cyclo (Pro-Tyr-D-Trp-t-4-AchxAla-Thr-Phe);
cyclo (Pro-Phe-D-Trp-t-4-AchxAla-Thr-Phe);
cyclo (N-Me-Ala-Tyr-D-Trp-Lys-Val-Phe);
cyclo (N-Me-Ala-Tyr-D-Trp-t-4-AchxAla-Thr-Phe);
cyclo (Pro-Tyr-D-Trp-4-Amphe-Thr-Phe);
cyclo (Pro-Phe-D-Trp-4-Amphe-Thr-Phe);
cyclo (N-Me-Ala-Tyr-D-Trp-4-Amphe-Thr-Phe);
cyclo (Asn-Phe-Phe-D-Trp-Lys-Thr-Phe-Gaba);
cyclo (Asn-Phe-Phe-D-Trp-Lys-Thr-Phe-Gaba-Gaba);
cyclo (Asn-Phe-D-Trp-Lys-Thr-Phe);
cyclo (Asn-Phe-Phe-D-Trp-Lys-Thr-Phe-NH(CH$_2$)$_4$CO);
cyclo (Asn-Phe-Phe-D-Trp-Lys-Thr-Phe-β-Ala);
cyclo (Asn-Phe-Phe-D-Trp-Lys-Thr-Phe-D-Glu)-OH;
cyclo (Phe-Phe-D-Trp-Lys-Thr-Phe);
cyclo (Phe-Phe-D-Trp-Lys-Thr-Phe-Gly);
cyclo (Phe-Phe-D-Trp-Lys-Thr-Phe-Gaba);
cyclo (Asn-Phe-Phe-D-Trp-Lys-Thr-Phe-Gly);
cyclo (Asn-Phe-Phe-D-Trp(F)-Lys-Thr-Phe-Gaba);
cyclo (Asn-Phe-Phe-D-Trp(NO$_2$)-Lys-Thr-Phe-Gaba);
cyclo (Asn-Phe-Phe-Trp(Br)-Lys-Thr-Phe-Gaba);
cyclo (Asn-Phe-Phe-D-Trp-Lys-Thr-Phe(I)-Gaba);
cyclo (Asn-Phe-Phe-D-Trp-Lys-Thr-Tyr(But)-Gaba);
cyclo (Bmp-Lys-Asn-Phe-Phe-D-Trp-Lys-Thr-Phe-Thr-Pro-Cys)-OH;
cyclo (Bmp-Lys-Asn-Phe-Phe-D-Trp-Lys-Thr-Phe-Thr-Pro-Cys)-OH;
cyclo (Bmp-Lys-Asn-Phe-Phe-D-Trp-Lys-Thr-Phe-Thr-Tpo-Cys)-OH;
cyclo (Bmp-Lys-Asn-Phe-Phe-D-Trp-Lys-Thr-Phe-Thr-MeLeu-Cys)-OH;
cyclo (Phe-Phe-D-Trp-Lys-Thr-Phe-Phe-Gaba);
cyclo (Phe-Phe-D-Trp-Lys-Thr-Phe-D-Phe-Gaba);
cyclo (Phe-Phe-D-Trp(5F)-Lys-Thr-Phe-Phe-Gaba);

cyclo (Asn-Phe-Phe-D-Trp-Lys(Ac)-Thr-Phe-NH-(CH$_2$)$_3$-CO);

cyclo (Lys-Phe-Phe-D-Trp-Lys-Thr-Phe-Gaba);

cyclo (Lys-Phe-Phe-D-Trp-Lys-Thr-Phe-Gaba); and cyclo (Orn-Phe-Phe-D-Trp-Lys-Thr-Phe-Gaba).

Also preferred somatostatin agonists of the invention is of the following formula:

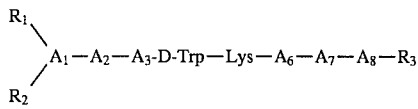

wherein A$_1$ is a D- or L-isomer of β-Nal, Trp, β-Pal, Phe, substituted Phe, or deleted; A$_2$ and A$_7$, independently, is Cys, Asp, or Lys, and are covalently linked either via a disulfide bridge or an amide bridge; A$_3$ is β-Nal, Phe, or o-, m-, or p-substituted X-Phe where X is a halogen, OH, NH$_2$, NO$_2$ or C$_{1-3}$ alkyl; A$_6$ is Val, Thr, Ser, Ala, Phe, β-Nal, Abu, Ile, Nle, or Nva; and A$_8$ is Phe, Thr, Tyr, Trp, Ser, β-Nal, —NH—CH(CH.[CH$_3$].OH)—CH$_2$— or deleted; each R$_1$ and R$_2$, independently, is H, lower acyl or lower alkyl; and R$_3$ is OH or NH$_2$; providing that when one of A$_2$ and A$_7$ is Cys, the other is also Cys, and that when neither of A$_2$ and A$_7$ is Cys, A$_2$ is different from A$_7$.

Particularly preferred somatostatin agonists of this formula to be used in the method of this invention include:

N-Me-D-Phe-Cys-Tyr-Tyr-D-Trp-Lys-Val-Cys-Thr-NH$_2$

D-Nal-Cys-Tyr-D-Trp-Lys-Thr-Cys-Nal-NH$_2$

Use of linear somatostatin agonists of the following formula is also within the invention:

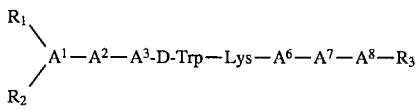

wherein

A$^1$ is a D- or L- isomer of Ala, Leu, Ile, Val, Nle, Thr, Ser, β-Nal, β-Pal, Trp, Phe, 2,4-dichloro-Phe, pentafluoro-Phe, p-X-Phe, or o-X-Phe, wherein X is CH$_3$, Cl, Br, F, OH, OCH$_3$ or NO$_2$;

A$^2$ is Ala, Leu, Ile, Val, Nle, Phe, β-Nal, pyridyl-Ala, Trp, 2,4-dichloro-Phe, pentafluoro-Phe, o-X-Phe, or p-X-Phe, wherein X is CH$_3$, Cl, Br, F, OH, OCH$_3$ or NO$_2$;

A$^3$ is pyridyl-Ala, Trp, Phe, β-Nal, 2,4-dichloro-Phe, pentafluoro-Phe, o-X-Phe, or p-X-Phe, wherein X is CH$_3$, Cl, Br, F, OH, OCH$_3$ or NO$_2$;

A$^6$ is Val, Ala, Leu, Ile, Nle, Thr, Abu, or Ser;

A$^7$ is Ala, Leu, Ile, Val, Nle, Phe, β-Nal, pyridyl-Ala, Trp, 2,4-dichloro-Phe, pentafluoro-Phe, o-X-Phe, or p-X-Phe, wherein X is CH$_3$, Cl, Br, F, OH, OCH$_3$ or NO$_2$;

A$^8$ is a D- or L-isomer of Ala, Leu, Ile, Val, Nle, Thr, —NH—CH(CH.[CH$_3$].OH)—CH$_2$—, Ser, Phe, β-Nal, pyridyl-Ala, Trp, 2,4-dichloro-Phe, pentafluoro-Phe, p-X-Phe, or o-X-Phe, wherein X is CH$_3$, Cl, Br, F, OH, OCH$_3$ or NO$_2$;

each R$_1$ and R$_2$, independently, is H, lower acyl or lower alkyl; and R$_3$ is OH or NH$_2$; provided that at least one of A$^1$ and A$^8$ and one of A$^2$ and A$^7$ must be an aromatic amino acid; and further provided that A$^1$, A$^2$, A$^7$ and A$^8$ cannot all be aromatic amino acids.

Particularly preferred linear agonists to be used in the method of this invention include:

H-D-Phe-p-chloro-Phe-Tyr-D-Trp-Lys-Thr-Phe-Thr-NH$_2$;

H-D-Phe-p-NO$_2$-Phe-Tyr-D-Trp-Lys-Val-Phe-Thr-NH$_2$;

H-D-Nal-p-chloro-Phe-Tyr-D-Trp-Lys-Val-Phe-Thr-NH$_2$;

H-D-Phe-Phe-Phe-D-Trp-Lys-Thr-Phe-Thr-NH$_2$;

H-D-Phe-Phe-Tyr-D-Trp-Lys-Val-Phe-Thr-NH$_2$;

H-D-Phe-p-chloro-Phe-Tyr-D-Trp-Lys-Val-Phe-Thr-NH$_2$;

H-D-Phe-Ala-Tyr-D-Trp-Lys-Val-Ala-β-D-Nal-NH$_2$;

If desired, one or more hydrophilic moieties (e.g., sugar derivative or ascorbic acid derivative) can be attached to the somatostatin agonist. See PCT Application WO 88/02756 and European Application 0 329 295 (1989), both of which are hereby incorporated by reference. Particularly preferred somatostatin agonists which contain hydrophilic moieties include:

N$^\alpha$-(α-glucosyl(1–4)-deoxyfructosyl)-D-Phe-Cys-Phe-D-Trp-Lys-Thr-Cys-threoninol Note that, unless indicated otherwise, for all somatostatin agonists described herein, each amino acid residue, e.g., Lys and A$^1$, represents the structure of NH—C(R)H—CO—, in which R is the side chain. Lines between amino acid residues represent peptide bonds which join the amino acids. Also, where the amino acid residue is optically active, it is the L-form configuration that is intended unless D-form is expressly designated. A disulfide bridge is formed between two Cys residues; however, it is not shown.

Synthesis of Somatostatin Agonists

The synthesis of an octapeptide somatostatin agonist with an amide C-terminus disclosed above follows. Other such octapeptides used in the invention can be prepared by making appropriate modifications, within the ability of someone of ordinary skill in this field, of the synthetic method disclosed herein.

The first step in the synthesis of H-D-β-Nal-Cys-Tyr-D-Trp-Lys-Val-Cys-Thr-NH$_2$ was preparation of the intermediate, tert-butyloxycarbonyl("Boc")-D-β-Nal-S-p-methylbenzyl-Cys-Tyr-D-Trp-ε-N-benzyloxycarbonyl-Lys-Val-S-p-methylbenzyl- Cys-O-benzyl-Thr-benzyhydrylamine resin, as follows.

Benzhydrylamine-polystyrene resin (Vega Biochemicals, Inc.) in the chloride ion form was placed in the reaction vessel of a Beckman 990B peptide synthesizer programmed to perform the following reaction cycle: (a) methylene chloride wash; (b) treatment with 33% trifluoroacetic acid in methylene chloride (two times, for 1 min. and 25 min. each); (c) methylene chloride wash; (d) ethanol wash; (e) methylene chloride; (f) treatment with 10% triethylamine in chloroform.

The neutralized resin was then stirred with Boc-O-benzyl-threonine and diisopropylcarbodiimide (1.5 mmole each) in methylene chloride for 1 hr. and the resulting amino acid resin was cycled through steps (a) to (f) in the above program. The following amino acids (1.5 mmole) were then coupled successively by the same procedure: Boc-S-methylbenzyl-Cys, Boc-Val, Boc-ε-N-benzyloxycarbonyl-Lys, Boc-D-Trp, Boc-Tyr, Boc-S-p-methylbenzyl-Cys, and Boc-D-β-Nal.

Thereafter, the resin was washed with methylene chloride, dried, and then mixed with anisole (4 ml) and anhydrous hydrogen fluoride (36 ml) at 0° C. and stirred for 45 min. Alternatively, one can also use thioanisole, trifluoroacetic acid, and trifluoromethane sulfonic acid at a ratio of 1:90:9, for 6 hr. Excess hydrogen fluoride was evaporated rapidly under a stream of dry nitrogen, the peptide and resin were treated with ether, and the resin and peptide were removed by filtration and washed with ether. The crude peptide thus obtained was then dissolved in 800 ml of 90% acetic acid to which was added $I_2$ in methanol until a permanent brown color appeared. The solution was then stirred for 1 hr. before removing the solvent under reduced pressure. The resulting oil was dissolved in a minimum volume of 50% acetic acid and placed on a Sephadex G-25 column (2.5×100 mm) which was then eluted with 50% acetic acid. Fractions containing a major component as shown by UV absorption and thin layer chromatography ("TLC") were then pooled, evaporated to a small volume, and applied to a column (2.5×50 cm) of Whatman LRP-1 octadecylsilane (15–20 µM).

The column was eluted with a linear gradient of 10–50% acetonitrile in 0.1% trifluoroacetic acid in water. Fractions were examined by TLC and analytical high performance liquid chromatography ("HPLC") and pooled to give maximum purity. TFA salt was prepared. Repeated lyophilization of the solution from water gave 170 mg of the product as a white, fluffy powder.

The product was found to be homogeneous by both HPLC and TLC. Amino acid analysis of an acid hydrolysate confirmed the composition of the octapeptide.

Also synthesized according to a method similar to that described above was, among others, H-D-Phe-Cys-Tyr-D-Trp-Lys-Thr-Cys-Nal-$NH_2$, another octapeptide analog of somatostatin with an amide C-terminus which can be employed for the treatment of cholangiocarcinoma.

The methods for synthesizing somatostatin agonists is well documented and are within the ability of a person of ordinary skill in the art. For example, synthesis of the peptide H-D-Phe-Cys-Phe-D-Trp-Lys-Thr-Cys-threoninol (octreotide) described above can be achieved by following the protocol set forth in Example 1A of U.S. Pat. No. 4,395,403, which is hereby incorporated by reference.

Assays for Determining Anti-Proliferative Activity

1. Tumor system

The human cholangiocarcinoma cell line SK-ChA-1 was grown from malignant ascites of a patient with primary adenocarcinoma of the extrahepatic biliary tree. See Knuth, et al. J. of Hepatology 1:579 (1985), hereby incorporated by reference.

2. Assay system

SK-ChA-1 cells were plated (100 µl) into 96-well culture plates (Falcon) at a density of 50,000 cells/ml in Dulbecco's modified Eagle's medium (DMEM/HAMSF12 (50:50)) with 2% fetal calf serum (FCS, Hyclone) and antibiotics (penicillin 100 IU/ml, streptomycin 100 µg/ml and amphotericin B 2.5 µg/ml). After 18 hours, the medium was replaced with fresh medium with or without the two test drugs, natural somatostatin-14 and the somatostatin agonist octreotide. The experiments were performed in triplicate. Wells without the addition of any test drug served as normal controls. All media, with the appropriate concentration of test drug, were changed every two days.

The amount of viable cells were assayed every two days using 3-(4,5-dimethylazol-2-yl)-2,5-diphenyl tetrazolium (MTT) according to method published by Tada, J. Immunol. Meth. 93:157 (1986), hereby incorporated by reference. Optical density was read by a 96-well automatic microplate reader (molecular Devices) at a test wavelength of 570 nm and a reference wavelength of 630 nm. An experiment had validated the correlation of the MTT assay (r=0.975, p=0.004) with a wide range of cell concentrations (3,000 to 330,000 cells/ml) counted with the hemocytometer. Cell proliferation curves with respect to time and test drug concentration were plotted with control wells as the baseline for comparison.

Two experiments were performed using this assay. The first experiment was performed at drug concentrations of $10^{-5}$M to $10^{-8}$M (in one log increments) and cell proliferation was assayed every two days until day 6. The second experiment was performed at concentrations of $10^{-5}$M to $10^{-10}$M (in one log increments) and assayed every two days until day 8.

3. Results

Table I shows the results of the first experiment, while Table II shows the results of the second experiment.

TABLE I

| Drug Concentration (M) | | Percent Protection, Day 8 |
|---|---|---|
| Somatostatin | $1 \times 10^{-5}$ M | 94.9 |
| | $1 \times 10^{-6}$ | 66.8 |
| | $1 \times 10^{-7}$ | 89.9 |
| Octreotide | $1 \times 10^{-5}$ | 79.1 |
| | $1 \times 10^{-6}$ | 92.2 |
| | $1 \times 10^{-7}$ | 78.4 |
| | $1 \times 10^{-8}$ | 61.0 |

TABLE II

| Drug Concentration (M) | | Percent Protection Day 4 |
|---|---|---|
| Somatostatin | $1 \times 10^{-5}$ | 54.3 |
| | $1 \times 10^{-6}$ | 47.5 |
| | $1 \times 10^{-7}$ | 42.6 |
| | $1 \times 10^{-8}$ | 50.2 |
| | $1 \times 10^{-9}$ | 50.4 |
| | $1 \times 10^{-10}$ | 62.3 |
| Octreotide | $1 \times 10^{-5}$ | 62.6 |
| | $1 \times 10^{-6}$ | 52.9 |
| | $1 \times 10^{-7}$ | 44.4 |
| | $1 \times 10^{-8}$ | 46.8 |
| | $1 \times 10^{-9}$ | 61.7 |
| | $1 \times 10^{-10}$ | 50.4 |

The results of these two anti-proliferation experiments are graphically depicted in FIGS. 1 and 2 (FIG. 1 graphs the results of the first experiment and FIG. 2 graphs the results of the second experiment). The X-axis of the figures depicts time in days. The Y-axis represents the percentage of the treated cell count to the control cell count. The two figures demonstrate that both somatostatin and octreotide are effective in inhibiting the growth of the human cholangiocarcinoma cell line. The observed non-dose dependency of both somatostatin and octreotide is inherent with this peptide series. See Setyono-Han, Cancer Research 47:1566 (1987) (demonstrating a lack of dose dependency for octreotide in MCF-7 breast cancer cells).

OTHER EMBODIMENTS

The foregoing description has been limited to specific embodiments of this invention. It will be apparent, however, that variations and modifications may be made to the invention, with the attainment of some or all of the advantages of the invention. Such embodiments are also within the scope of the following claims.

What is claimed is:

1. A method of inhibiting proliferation of bile duct epithelium, said method comprising the step of contacting said epithelium with an effective amount of somatostatin or a somatostatin agonist.

2. The method of claim 1, wherein said proliferation is benign tumor growth.

3. The method of claim 1, wherein said proliferation is malignant tumor growth.

4. The method of claim 1, wherein said contacting is effected parentally.

5. The method of claim 4, wherein said contacting is effected intravenously.

6. The method of claim 4, wherein said contacting is effected subcutaneously.

7. The method of claim 4, wherein said contacting is effected by implantation.

8. The method of claim 4, wherein said contacting is effected by perfusion.

9. The method of claim 2, wherein said contacting is effected parentally.

10. The method of claim 9, wherein said contacting is effected intravenously.

11. The method of claim 9, wherein said contacting is effected subcutaneously.

12. The method of claim 9, wherein said contacting is effected by implantation.

13. The method of claim 9, wherein said contacting is effected by perfusion.

14. The method of claim 3, wherein said contacting is effected parentally.

15. The method of claim 14, wherein said contacting is effected intravenously.

16. The method of claim 14, wherein said contacting is effected subcutaneously.

17. The method of claim 14, wherein said contacting is effected by implantation.

18. The method of claim 14, wherein said contacting is effected by perfusion.

* * * * *